United States Patent [19]

Akhtar

[11] Patent Number: 5,148,822
[45] Date of Patent: Sep. 22, 1992

[54] HAIR STRAIGHTENING METHOD AND TEXTURING STRENGTHENER COMPOSITIONS THEREFOR

[75] Inventor: Muhammad M. Akhtar, Bolingbrook, Ill.

[73] Assignee: Johnson Products Co., Inc., Chicago, Ill.

[21] Appl. No.: 781,717

[22] Filed: Oct. 22, 1991

Related U.S. Application Data

[63] Continuation of Ser. No. 95,397, Sep. 10, 1987, Pat. No. 5,060,680.

[51] Int. Cl.⁵ .............................................. A45D 7/04
[52] U.S. Cl. ................................... 132/204; 132/205
[58] Field of Search .................. 132/204, 205; 424/70, 424/71

[56] References Cited

U.S. PATENT DOCUMENTS

Re. 30,874  3/1982  Dasher et al. .
Re. 31,126  1/1983  Dasher et al. .
3,958,581  5/1976  Abegg et al. .
4,175,572  11/1979  Hsiung et al .
4,237,910  12/1980  Khalil et al. .
4,304,244  12/1981  de la Guardia .
4,361,157  11/1982  James .
4,369,037  1/1983  Matsunaga et al. .
4,416,297  11/1983  Wolfram et al. .
4,507,280  3/1985  Pohl et al. .
4,602,648  7/1986  Syed et al .
4,663,158  5/1987  Wolfram et al. .

OTHER PUBLICATIONS

Finkelstein, et al., "The Mechanism of Conditioning of Hair with Alkyl Quarternary Ammonium Compounds," App. Polym. symp. 18, 673 (1971).
Cook "Modern Negro Cosmetics II" DCI 106, 42-44 (May) 1970.
Brooks et al., "Treatment Regimens for 'Styled' Black Hair," Cosm. & Toilet, 98 pp. 59-68 (May) 1983.
Sykes, "The Use of Merquat Polymers," DCI, 126, 62 (1980).

Primary Examiner—V. Millin
Attorney, Agent, or Firm—Olson & Hierl, Ltd.

[57] ABSTRACT

This invention relates to a method of straightening, texturing and strengthening hair undergoing an alkaline straightening procedure and to nonacidic aqueous hair texturing and strengthening compositions for use in conjunction therewith. The texturing and strengthening compositions have a pH value from at least 8 to about 11 containing at least one water-dispersible hair texturing and strengthening agent including a quarternary nitrogen atom with at least one aliphatic alkyl group directly or indirectly bonded to the quarternary nitrogen atom, the aliphatic alkyl group having from about 3 to about 22 carbon atoms. Methods for applying the compositions in post-straightening and pre-straightening procedures are disclosed.

18 Claims, No Drawings

HAIR STRAIGHTENING METHOD AND TEXTURING STRENGTHENER COMPOSITIONS THEREFOR

CROSS REFERENCE TO RELATED APPLICATION

This application is a continuation of co-pending application Ser. No. 095,397, filed Sep. 10, 1987, now identified as U.S. Pat. No. 5,060,680.

TECHNICAL FIELD

This invention relates to the art of chemically straightening human hair and to texturing strengthener compositions for use in conjunction with alkaline hair straighteners. More particularly, non-acidic compositions are provided which contain a cationic texturing strengthening agent to simultaneously texturize and strengthen hair undergoing a highly alkaline straightening procedure.

BACKGROUND OF THE INVENTION

Until now, practitioners of chemical hair straightening arts have been unable to successfully increase and maintain negatively-charged cation receptive sites in alkali-straightened (relaxed) hair to simultaneously strengthen and restore its textural quality to that substantially resembling hair in relatively good condition.

Most commonly used relaxers are based on hydroxide-containing alkalis, sulfites or thioglycolates. Of these, the most effective and popular are alkaline straightener compositions that produce stable lanthionine linkages in the hair. These chemical hair straighteners usually contain relatively strong alkalis, such as sodium hydroxide, potassium hydroxide, calcium hydroxide, lithium hydroxide and guanidine hydroxide. The highly alkaline conditions (pH 12 to 14) of these products, however, causes a substantial amount of swelling in human hair. Consequently, some hydrolysis of the polypeptide chains in the hair protein at about pH 12.5 is inevitable.

Prolonged or unnecessary exposure of hair to a strong alkali weakens, breaks and even dissolves the hair. Thus, it is an accepted practice to minimize the time that the hair is exposed to highly alkaline hair straighteners. Towards this end, substantially all the straightener is immediately rinsed from the hair as soon as the desired partial or complete straightening effect is achieved. Further, to remove any residual hair straightener remaining in the rinsed hair, and to deswell the hair, an acidic neutralizer is applied immediately thereafter to the rinsed alkali-treated hair. Generally this acidic neutralizer is a nonalkaline shampoo or an acid rinse having a pH below 7, usually in a pH range between about 1 to about 6 and preferably close to the isoelectric region of human hair, approximately pH 4.

Some success in preventing further alkali attack on the hair is achieved by deswelling the hair in the foregoing manner. However, the textural quality of acid-treated hair is harsh and strawlike, unless known conditioners are included in the shampoo or rinse. The term "conditioners" refers to cosmetically useful emollients, such as oils, quaternary ammonium salts, cationic polymers and the like, known to those skilled in hair conditioning art.

It is known that human hair is negatively charged, i.e., more anionic, above its isoelectric region, and hence, more receptive to adsorbing cationic materials. There is also some indication that the cationic qualities of certain quaternary ammonium salts are enhanced under alkaline conditions. Finkelstein, et al., "The Mechanism of Conditioning of Hair with Alkyl Quaternary Ammonium Compounds," *App. Polym. Symp.*, 18, 673 (1971), for example, report that the cationic properties of stearyltrimethyl ammonium chloride are greater at pH 7.5 than at pH 4.5. However, any attempt to enhance or sustain the cation-receptivity of alkali-straightened hair by further exposing it immediately to a non-acidic composition having a pH greater than 7 is generally avoided.

Thus, the non-polymeric quaternary ammonium salts often used for hair conditioning are employed at relatively low pH values rather than at higher pH values. Under alkaline conditions, such compounds tend to deposit an unacceptable delustering coating on the hair. Also, because of their relatively small molecular size, they are easily removed from the hair so conditioning benefits obtained are temporary.

As a result, cationic polymers, especially those containing quaternary nitrogen atoms, are more often used in hair conditioning compositions, because these polymers are usually substantive to hair at acidic pH values. The term "substantive" cannot be defined by distinctive physicochemical properties, but involves mechanisms such as adsorption, ion exchange and chemical interaction. As used herein, the term "substantive" or its grammatical variant "substantivity" refers to the retention of a cationic material deposited or adsorbed on the hair through several shampoo applications.

Not all cationic polymers, however, are alkali-compatible or stable under alkaline conditions. Some cationic polymers must first be complexed with some anionically active component already present on the hair or in the neutralizing shampoo to form a conditioning reaction product.

Proteinaceous materials that are water-soluble and substantive to hair are also known desirable compounds. A number of water-soluble hydrolyzed protein compounds are commercially available, some of which display cationic qualities under acidic conditions. However, their utility under alkaline conditions is limited, because they become neutral or anionic in character and some degradation of the amide groups in the protein portion takes place. Consequently, their use in non-acidic compositions is generally avoided.

Prior attempts have been limited, therefore, to applying conditioners under acidic or neutral conditions to at least improve the tactile feel, if not the strength of the alkali-straightened hair.

In one approach, a non-alkaline composition containing one or more of the foregoing conditioners is applied to the hair before the hair straightener. However, one drawback of this approach is that any conditioning benefit achieved generally does not survive the subsequent highly alkaline chemical straightening procedure. In addition, these conditioners may weaken the strength of the hair straightener product or interfere with its effectiveness.

This drawback was partially overcome by including a quaternary nitrogen-containing cationic polymer in the alkaline hair straightener product as described in U.S. Pat. No. 4,175,572. Such a product is presently marketed. However, the residual alkalinity in the hair following use of this product is substantially immediately neutralized by application of a non-alkaline neutralizing shampoo.

In another approach, a conditioning nonalkaline shampoo neutralizer is employed immediately after rinsing the straightener from the hair with water. However, a shampoo, by the manner in which it must be used, contacts the hair too briefly to maximize adsorption of cationic materials. Further, alkali-weakened hair may not withstand the manipulative actions inherently required for the shampooing process so some hair loss or breakage can occur.

U.S. Pat. No. 4,602,648 (hereafter the '648 patent) discloses the use of hydrolyzed proteins and/or cationic polymers in a "pre-shampoo normalizer" so-called because it is applied between the straightening step and the shampooing step. Several products following such a procedure are presently being marketed. However, the effectiveness of such normalizer compositions suffers the same drawbacks of prior acidic compositions.

The pre-shampoo normalizers of the '648 patent are acidic or nonalkaline compositions that are adjusted by the addition of acid to a pH of between 2.5 and 7. Thus, these compositions decrease, rather than increase, cation-receptive negatively-charged sites in the hair as the acidity of the composition neutralizes the alkaline residue in the hair. Thus, this approach constitutes, in effect, an acidic neutralization procedure, because the '648 patent normalizer step is followed by a shampooing step to remove both residual straightener and residual normalizer composition from the hair.

The '648 patent purports to take advantage of the sensitive state of the hair at a relatively high alkaline pH of between about 9 and 11 after the straightener treatment to mediate damage and improve the aesthetic qualities of the straightened hair. However, we have found from experience that when the method of this patent is followed, substantive conditioning and strengthening are not simultaneously achieved. This was determined by measuring the strength and subjective textural qualities of the straightened hair.

There is a need for a relatively simple method and a product that simultaneously strengthen and enhance the cation-receptivity of hair undergoing or about to undergo a highly alkaline hair straightening procedure. We have now surprisingly found that the cation-receptivity of alkali-straightened hair can be enhanced and sustained, while the hair is simultaneously strengthened, by applying the non-acidic compositions of this invention to hair in a post-straightening and pre-straightening step. The hair straightening method and texturing strengthener compositions of this invention satisfy that need.

SUMMARY OF THE INVENTION

This invention relates to a method of simultaneously straightening, texturing and strengthening hair undergoing an alkaline straightening procedure, and particularly to non-acidic aqueous texturing and strengthening compositions for use in conjunction with such highly alkaline hair straighteners.

The term "highly alkaline" used in connection with hair straighteners refers to products that contain alkaline straightening agents that provide a pH value of about 12 to about 14. These are generally known to those skilled in the hair straightening art as "lye" and "no-lye" relaxers. The term "non-acidic", as applied to compositions of this invention, relates to vehicles containing no ionizable hydrogen-containing substances capable of neutralizing residual alkali on the hair from the hair straightener product.

In one embodiment of the method of this invention, a texturing and strengthening agent contained in an aqueous composition having a pH of from between at least 8 to about 11 is applied in a post-straightening step, as disclosed herein, to enhance and sustain cation receptive negatively-charged sites in hair which has just undergone an alkali straightening procedure. The post-straightening step follows substantially immediately after the hair straightener is rinsed from the hair.

In another embodiment, the above method includes applying an auxiliary amount of the texturing and strengthening agent contained in an aqueous texturing and strengthening composition in a pre-straightening step to hair about to undergo the straightening procedure. An auxiliary amount refers to an amount of hair texturing and strengthening agent applied to either the virgin outgrowth portion or previously treated outgrowth portion of the hair in addition to the amount of hair texturing and strengthening agent applied in the post-straightening step. The pre-straightening step is substantially immediately before the hair straightener is applied to the hair. The auxiliary amount of hair texturing and strengthening agent applied to the hair in the pre-straightening step can be provided in a non-acidic aqueous composition that is the same or different from that applied in the post-straightening step.

Texturing and strengthening is substantially achieved within about 5 minutes of the post-straightening step. However, the method includes a shampooing step to cleanse the hair and scalp of residual hair straightener, if any, and excess texturing and straightening composition.

The term "texturing" or its grammatical variant "texturize" refers to those physical, chemical and mechanical characteristics of hair associated with subjectively discernible changes in the textural qualities of the hair and its tensile strength.

The terms "strength" and "strengthening" as used in connection with alkali-straightened hair refer to changes in mechanical properties of hair fibers related to the overall dynamic and static moduli of a hair fiber, as measured by stress-strain and breaking force techniques. Loss of strength and swelling are generally associated in straightened hair with weakened fiber integrity, such that the alkali-straightened hair can break during shampooing or combing. Weakened hair is also associated with poor textural qualities (spongy, rubbery) that negatively affect its hand.

The term "hand", as used herein, refers to the subjective feel of the hair or tactile reaction to such textural qualities as smoothness, softness and flexibility when the hair is combed or manipulated during styling. The term "fiber integrity" as used herein includes those physical and chemical characteristics of intact hair subjectively associated with the mechanical properties of hair condition, i.e., easy combability, manageability and hand.

We have surprisingly found that hair undergoing a highly alkaline straightening procedure can be simultaneously textured and strengthened by aqueous texturing and strengthening compositions of this invention which have a pH of at least 8 or greater and contain certain cationic hair texturing and strengthening agents.

In one embodiment, an aqueous hair texturing and strengthening composition of this invention has a pH value from at least 8 to about 11, preferably from at least 8 to about 9. The composition includes at least one water-dispersible hair texturing and strengthening agent including a quaternary nitrogen atom with at least one aliphatic alkyl group directly or indirectly bonded to the quaternary nitrogen atom. The aliphatic alkyl group has from about 3 to about 22 carbon atoms. For achieving the desired pH, the compositions can include a base.

Suitable water-dispersible texturing and strengthening agents include quaternary ammonium derivatives of a hydrolyzed animal protein and quaternary nitrogen-containing compounds including at least one aliphatic alkyl group bonded directly or indirectly to the quaternary nitrogen atom. Each alkyl group preferably contains from about 8 to about 18 carbon atoms and the remainder of the groups bonded to the quaternary nitrogen atom include alkyl groups having from 1 to about 4 carbon atoms, a benzyl radical and combinations thereof. The term "water-dispersible", as used herein in connection with cationic materials, includes water-soluble compounds that form substantially clear solutions when dispersed or dissolved in water.

In a preferred embodiment of the composition, the hair texturing and strengthening agent is a quaternary ammonium derivative of a hydrolyzed collagen protein in which over about 70 percent of the available amino groups have been quaternized to incorporate at least one aliphatic alkyl group having from about 3 to about 18 carbon atoms in the aliphatic alkyl group. A particularly preferred quaternary ammonium derivative of hydrolyzed collagen protein incorporates from about 12 to about 18 carbon atoms in at least one aliphatic alkyl group, has a weight average molecular weight from about 2500 to about 12,000, and has an isoionic point from about 9.5 to about 11.5.

For augmenting the texturing effect on alkali-straightened hair, a hair texturing and strengthening composition of this invention includes a water-dispersible cationic polymer. The term "cationic polymer" as used herein includes quaternized polymers containing at least one positively charged nitrogen atom in each repeating unit of the polymer chain, unquaternized polymers having tertiary amino nitrogen groups that become quaternized when protonated and corresponding copolymers thereof. A particularly preferred polymer is a polydiallyldialkyl ammonium chloride homopolymer in which the alkyl group contains from 2 to 3 carbon atoms, and the polymer has a weight average molecular weight of about 100,000.

The methods and compositions of this invention have many advantages and benefits. One advantage is that the cation receptivity of alkali-treated hair is enhanced and sustained to strengthen the hair while shampoo resistant texturing benefits are provided. Another benefit is that compositions can be applied to previously untreated virgin growth portions of the hair to make the hair more cation-receptive prior to undergoing the alkaline straightening procedure. Yet another benefit is that previously straightened outgrowth portions of the hair can also be textured with non-acidic compositions without interfering with the subsequent alkaline straightening procedure.

Still further benefits and advantages of the present invention will become apparent to those skilled in the art from the detailed description of the invention, the examples and the claims that follow.

DETAILED DESCRIPTION OF THE INVENTION

The method of this invention provides for texturing and strengthening hair about to undergo or having just undergone an alkaline hair straightening (relaxing) procedure. Such compositions typically contain as the active hair straightening agent relatively strong alkalis such as sodium hydroxide, potassium hydroxide, calcium hydroxide, lithium hydroxide, guanidine hydroxide and quaternary ammonium hydroxide. For convenience, hair that has undergone a highly alkaline hair straightening procedure at a pH of about 12 to about 14 is referred to herein simply as alkali-straightened hair or relaxed hair.

The mechanism of simultaneously texturing and strengthening alkali-straightened hair by compositions of this invention is not fully understood. We believe that negatively charged sites in alkali-straightened hair are sustained by compositions of this invention having a pH of at least 8 resulting in enhanced cation substantivity on the hair without impairing fiber integrity. The available positively charged sites in the texturing and strengthening agent may bind to the negatively charged sites in the hair to provide a discernible improvement in the textural qualities of the alkali-straightened hair that lasts through subsequent shampoo procedures. Further, the strength of the alkali-treated hair simultaneously improves as measured by break force and intermittent stress strain modulus techniques described below. However, the effectiveness of the present methods and compositions does not depend upon and is not limited by the foregoing description of a proposed mechanism.

The texturing and strengthening agent of this invention is a water-dispersible quaternary nitrogen-containing compound having at least one aliphatic alkyl group directly or indirectly bonded to a quaternary nitrogen atom. The aliphatic alkyl group preferably includes from about 3 to about 22 carbon atoms. Particularly preferred aliphatic alkyl groups are lipophilic fatty acid derivatives of a natural or synthetic fatty acid or a source of fatty acids, either linear or branched, containing from about 12 to about 18 carbon atoms.

Suitable texturing and strengthening agents are proteinaceous and nonproteinaceous quaternary ammonium compounds. These compounds include quaternary ammonium derivatives of a hydrolyzed animal protein and quaternary nitrogen-containing compounds including at least one aliphatic alkyl groups bonded directly or indirectly to the quaternary nitrogen atom. Each alkyl group preferably contains from about 8 to about 18 carbon atoms and the remainder of the quaternary nitrogen bonds include alkyl groups having from 1 to about 4 carbon atoms, a benzyl radical and combinations thereof.

Preferably, the quaternary nitrogen of the quaternary ammonium compound retains its positive charge and is stable at an alkaline pH in the range of at least pH 8 to about 11. Especially preferred are quaternary ammonium compounds that are substantive to hair and which disperse in water to provide solutions that are substantially clear at a pH above 8.

Examples of water-dispersible proteinaceous quaternary ammonium compounds include derivatives of chemically-modified hydrolyzed animal protein, such as quaternary ammonium derivatives of hydrolyzed collagen protein including at least one aliphatic alkyl group having from about 12 to about 18 carbon atoms in the aliphatic alkyl group. Compounds of this type that are commercially available include the following compositions aid by Croda, Inc., New York, N.Y.: lauryldimethylammonium hydrolyzed animal protein (trade name CROQUAT L); coconutdimethylammonium hydrolyzed animal protein (trade name CROQUAT M); stearyldimethylammonium hydrolyzed animal protein (trade name CROQUAT S); stearyltrimethylammonium animal protein (trade name CROTEIN Q); and the following compositions sold by Inolex Chemical Company, Philadelphia, Pa.: cocoamidodimethylhydroxypropylamino hydrolyzed animal protein (trade name LEXEIN QX3000) and oleamidopropyldimethylamine hydrolyzed animal protein (trade name LEXEIN CP125). Another illustrative quaternary ammonium derivative of collagen protein that includes an aliphatic alkyl group containing 3 carbon atoms is commercially available from Hormel, Oak Brook, Ill., under the name PROLAGEN MP-1. The foregoing list is intended to be illustrative and not limiting.

Particularly preferred is the quaternary ammonium derivative of hydrolyzed collagen protein sold under the trade name CROQUAT M by Croda, Inc. This compound, and the structurally related CROQUAT L and CROQUAT S derivatives, are reported to have at least 70 percent of the available amino acid groups in the collagen quaternized. Thus, these compounds are alkyl dimethyl ammonium chloride derivatives having a plurality of quaternary nitrogen-containing alkyl dimethyl moieties covalently bonded directly to the peptide chain and are reported to have a hydroxyproline content of about 4.5 percent to about 6 percent. The Croquat materials reportedly have an isoionic point in the range of about 10 to about 11.5 and retain their net positive charge at a pH value of about 9.5.

Likewise, another preferred quaternary ammonium derivative of hydrolyzed collagen protein is sold under the trade name CROTEIN Q by Croda, Inc. This material is reported to have over 90 percent of its available amino acid groups quaternized and the amino acid residues are indirectly bonded to a quaternary nitrogen atom by an 18 carbon aliphatic alkyl chain. The aliphatic alkyl chain including the hydrolyzed protein is directly bonded to a quaternary nitrogen atom with the remaining quaternary nitrogen bonds taken up with methyl groups. CROTEIN Q is reported to have a isoionic point in the range of about 9.5 to about 10.5 and is positively charged at all pH values up to an isoelectric point of about 10.

The term "isoionic point" refers to the pH range in which the proteinaceous quaternary ammonium compound is ionically charged. The term "isoelectric point" refers to the pH at which the proteinaceous quaternary ammonium compound has no net charge.

Non-proteinaceous water-dispersible quaternary nitrogen-containing compounds containing at least one aliphatic alkyl group bonded directly or indirectly to the quaternary nitrogen atom include quaternary ammonium compounds in the form of a salt having a substantially innocuous inorganic or organic anion such as a halide, preferably chloride or bromide, sulfate, sulfite, phosphate, nitrate, nitrite, acetate, methylsulfate, ethosulfate and toluenesulfonate.

Illustrative examples of non-proteinaceous water-dispersible quanternary nitrogen-containing compounds include octyltrimethyl ammonium chloride; decyltrimethyl ammonium chloride; lauryldimethylethyl ammonium chloride; lauryltrimethyl ammonium chloride; cetyldimethylethyl ammonium chloride; cetyltrimethyl ammonium chloride; tetradecyltrimethyl ammonium chloride; stearyltrimethyl ammonium chloride; 3-behenoyloxy-2-hydroxypropyltrimethyl ammonium chloride; behenyltrimethyl ammonium chloride; behenyltrimethyl ammonium methosulfate. Also suitable are dialkyldimethyl ammonium chlorides wherein each of the alkyl groups is a saturated group having from about 8 to about 18 carbon atoms, such as distearyldimethyl ammonium chloride; dilauryldimethyl ammonium chloride, didecyldimethyl ammonium chloride; di-(hydrogenated tallow)-dimethyl ammonium chloride. Mixed higher alkyl trimethyl ammonium chlorides containing mixtures of predominantly long-chain aliphatic alkyl radicals having from about 8 to about 18 carbon chains in the alkyl group may also be used such as derivatives of coconut oil, tallow, soya bean oil, cottonseed oil, babassu oil, palm oil, etc. Compounds that correspond to the foregoing may also be employed where the anion is other than a halide, as noted above.

A particularly preferred non-proteinacious water-dispersible quaternary nitrogen-containing compound has the CTFA adopted name of dicetyldimonium chloride and is an N-hexadecyl-N,N-dimethyl-1-hexadecaminium chloride corresponding to the commercial material sold under the trade name ADOGEN 432CG by Sherex Chemical Company, Inc., Dublin, Ohio.

Additional illustrative quaternary ammonium compounds include "benzyl quats" such as aliphatic alkyldimethylbenzyl ammonium chlorides having from about 8 to about 18 carbon atoms in the aliphatic alkyl group. These compounds include cetyldimethylbenzyl ammonium chloride; stearyldimethylbenzyl ammonium chloride; tetradecyldimethylbenzyl ammonium chloride; cetyldimethylbenzyl ammonium chloride; n-dodecyldimethyl-p-chlorobenzyl ammonium chloride; laurylpyridinium chloride; cetylpyridinium chloride; alkyl isoquinolinium chlorides or bromides having about 8 to about 18 carbon atoms in the alkyl chain, such as laurylisoquinolinium chloride; N-(acyl-colaminoformylmethyl)-pyridinium chlorides and bromides wherein the acyl radical contains from 8 to 18 carbon atoms, such as octoyl, lauroyl, palmitoyl and stearoyl, and the like. Another exemplary material is N-soya-N-ethyl morpholinium ethosulfate, such as the material sold under the trade name ATLAS G271 by ICI Americas, Inc., Wilmington, Del. This listing is by way of illustration and is not intended to be limiting.

For practicing the method of this invention, the compositions contain at least one or more texturing and strengthening agents. Preferred compositions contain at least one quaternary ammonium derivative of a hydrolyzed protein as the texturing and strengthening agent.

For practicing the principles of this invention, an effective amount of a texturing and strengthening agent is dispersed in water with sufficient base, if needed, to adjust the pH of the composition to between at least pH 8 to about pH 11, preferably from at least pH 8 to about pH 9, more preferably from about pH 8.1 to about pH 8.5.

An effective amount of total texturing and strengthening agents present is from about 0.1 percent to about 8 percent by weight, preferably from about 0.2 percent to about 6.0 percent by weight, and more preferably from about 0.5 percent to about 5.0 percent by weight. Percent by weight as used herein refers to the weight of active dry solids based on the total weight of the composition. It is recognized that actual suitable amounts are limited only by the solubility or dispersibility of a selected compound in water and by economic considerations. It is also recognized that amounts greater than 8 percent can be used, but such amounts are believed unnecessary and wasteful.

Bases suitable for adjusting the pH of the compositions include alkali metal hydroxides, and lower alkyl organic bases in which the alkyl group contains from 1 to about 6 carbon atoms commonly employed in the cosmetic arts. While it is recognized that a volatile base, such as ammonia, as well as the foregoing nonvolatile bases, can be used for purposes of achieving the desired pH, ammonia is not preferred to avoid swelling the alkali-treated hair or irritating the skin.

Exemplary alkali metal hydroxides include sodium hydroxide and potassium hydroxide. The amount of sodium hydroxide employed is relatively small for adjusting the pH and, thus, is well below the amounts normally used in hair straighteners.

Exemplary lower alkyl organic bases include primary alkylamines such as ethylamine or propylamine; secondary alkylamines such as diethylamine, morpholine or ethylpropylamine; tertiary amines such as triethylamine or quinuclidine; and preferably a hydroxyalkylamine containing 2 to 6 carbons per alkyl group bonded to the amine nitrogen atom such as monoethanolamine, diethanolamine, triethanolamine, monoisopropanolamine, diisopropanolamine, triisopropanolamine, 2-amino-1-butanol, 1-amino-2-methyl-2-propanol and 2-amino-2-methyl-1-propanol. A particularly preferred base is triethanolamine.

For purposes of augmenting the texturing effect on alkali-straightened hair, a water-dispersible cationic polymer can be included in compositions of this invention. Suitable cationic polymers preferably include quaternized polymers containing at least one positively charged nitrogen atom in each repeating unit of the polymer chain, but can include unquaternized polymers that behave like cationic polymers when protonated and corresponding copolymers of the foregoing. Preferably, cationic polymers useful in compositions of this invention retain their cationic positive charge at a pH above at least 8, provide substantially clear solutions when dispersed in water and are substantive to hair.

Broadly, cationic polymers are useful in concentrations of about 0.01 percent to about 5 percent by weight, preferably in amounts of about 0.1 percent to about 3.5 percent by weight, and more preferably in amounts of about 0.2 to about 2.5 percent by weight. The percentage is expressed as the weight of dry solids based on the total weight of the composition. The weight average molecular weights of the polymers useful herein are broadly between about 3000 and about 10,000,000, with various useful polymers having a generally more narrow average molecular weight range.

A number of cationic polymers, their manufacturers and general description of their composition can be found in the CTFA Cosmetic Ingredient Dictionary, 3rd ed., 1982 and in the CTFA Cosmetic Ingredient Dictionary, 3rd ed., Supplement, 1985, both published by the Cosmetic Toiletry and Fragrance Association, Inc. (CTFA) and incorporated herein by reference. The official CTFA name assigned to ingredients appearing therein or as assigned by the manufacturer, when known, will be employed for convenience.

Preferred cationic polymers include those prepared from polydiallyldialkylammonium salts containing from 2 to 3 carbon atoms in the alkyl group. The preparation of these polymers is described in U.S. Pat. Nos. 3,288,770 and 3,412,019. These polymers are sold commercially under the trade name MERQUAT by Merck & Company, Inc., Rahway, N.J. Particularly preferred is a polydiallyldimethylammonium chloride homopolymer designated polyquaternium-6 by the CTFA and sold under the trade name MERQUAT-100. This polymer is described as having a weight average molecular weight of approximately 100,000 and is supplied as a 40 percent aqueous solution. Also preferred is a copolymer of diallyldimethylammonium chloride with acrylamide designated polyquaternium-7 by the CTFA and sold under the trade name MERQUAT-550. This material is described as having a weight average molecular weight of approximately 500,000 and is supplied as an 8 percent aqueous solution. A discussion of these materials and their properties is found in Sykes et al., "The Use of Merquat Polymers," *Drug Cosm. Ind.*, 126, 62 (1980) which is incorporated herein by reference.

Other useful cationic polymers are quaternary ammonium derivatives of natural guar gum assigned CTFA names of guar hydroxypropyltrimonium chloride. Natural water-soluble polymers of cationic guar that are compatible over a wide pH range of from about 3 to about 11 are commercially available, sold under the trade names JAGUAR C-13, C-14-8, C-15 and C-17 by Celanese Corporation, Louisville, Ky. Guar is a galactomannan with a structure composed of a straight backbone chain of D-mannopyranose units with a side branching unit of D-galactopyranose on every other unit and having an average molecular weight in the range of about 200,000 to about 300,000. A description of these cationic gums is found in Freeland et al., "Cationic Guar Gum," *Cosmet. Toilet.*, 99, 83 (1984) which is incorporated herein by reference.

A listing of useful cationic polymers which is not intended to be exhaustive or limiting follows:

adipic acid/epoxypropyl diethylenetriamine copolymer (sold by Hercules Inc., Wilmington, Del., under the name DELSETTE 101);

adipic acid/dimethylaminohydroxypropyldiethylenetriamine copolymers (sold by Sandoz Chemicals Corporation, Charlotte, N.C., under the name CARTARETIN);

polyquaternium-2, a poly[N-(3-dimethylamino) propyl]-N'-[3-(ethyleneoxyethylene dimethylamino)-propyl]urea dichloride (sold by Miranol Chemical Company, Inc., Dayton, N.J. under the name Mirapol A 15);

quaternary ammonium polymers formed by the reaction of dimethyl sulfate and a copolymer of vinyl pyrrolidone and N,N-dimethylaminoethylmethacrylate (sold by GAF Corporation, Wayne, N.J. under the names GAFQUAT-734 and GAFQUAT-755); polymers of hydroxyethyl cellulose reacted with epichlorohydrin and quaternized with trimethylamine (sold by Union Carbide Corporation, Danbury, Conn. under the trademark POLYMER JR and available in a range of various molecular weight sizes);

copolymers prepared from acrylamide and N,N-dimethylaminoethyl methacrylate and quaternized with dimethyl sulfate (sold by Hercules, Inc. under the name RETEN);

aminoethylacrylate phosphate/acrylate copolymer (sold by National Starch & Chemical Corporation, Bridgewater, N.J., under the name CATREX);

polyquaternium-1 a polymeric quaternized dimethylbutenyl ammonium chloride terminated with quaternized triethanolamine groups (sold by Onyx Chemical Company, Jersey City, N.J., under the name ONAMER M);

poly(methacrylamidopropyltrimethyl ammonium chloride) obtained by the polymerization of the corresponding monomer sold by Texaco Chemical Company, Bellaire, Tex. under the name MAPTAC; and quaternized poly(ethyleneimine), quaternized poly(vinylamine), quaternized poly-4-vinyl pyridine and the like prepared by methods generally known in the art.

Thus, a useful texturing and strengthening composition of this invention can include from zero to about 5 percent by weight of cationic polymer. Amounts greater than 5 percent can be employed but are considered unnecessary and wasteful. Additionally, the compositions can contain any of a variety of cosmetically known adjuvants, including emulsifiers, preservatives, viscosity modifying thickeners, auxiliary solvents such as alcohols or glycols, proteins, perfume and the like.

It is recognized that some emulsifiers and some quaternary ammonium compounds may have some surface active characteristics useful for distributing the composition through the hair during application. However, surface active agents typically associated with foaming shampoo products are not necessary for practicing the texturing and strengthening aspects of this invention. Texturing is independent of any interaction between the texturing and strengthening agent and any surface active component and does not depend on any co-reaction therebetween. Thus, texturing and strengthening compositions are preferably substantially free of foam-producing surface active agents.

In the method of this invention, highly alkaline hair straightener products are applied to the hair by methods well known in the art to at least partially straighten those portions of the hair that have received no prior chemical hair straightening treatment, i.e., substantially virgin outgrowth. It is generally well known that the length of time that the hair is exposed to a highly alkaline straightener or relaxer product varies with the amount of curl in the hair and the strength of the alkaline straightening agent. Typically, this length of time is determined by the practitioner based on the amount of partial or complete removal of natural curl desired. Less than about 20 minutes, preferably less than about 15–18 minutes, is desirable.

For purposes of texturing and strengthening the alkali-treated hair, substantially all the hair straightener product is removed from the hair, preferably by rinsing with water. Substantially immediately thereafter, a post-straightening amount of texturing and strengthening composition is applied. For this purpose, the composition has a pH of from between at least 8 to about 11, and preferably from between at least pH 8 and about pH 9 as described above. The composition is applied in an amount sufficient to contact the hair fibers when it is stroked through the hair in a gentle downward motion from the scalp to the end portions. A sufficient amount was found to be about 1 ounce per average head of hair.

Surprisingly, we have found that such a post-straightening application of a non-acidic composition of this invention having a pH value of at least 8 or higher had no adverse effect on the physical integrity of such recently alkali-treated hair. This finding is contrary to what would normally be expected and is contrary to what is presently practiced. Also, surprising, we found that hair contacted in this manner for a relatively short time of about 5 minutes was simultaneously textured and strengthened and had decreased residual alkalinity.

Residual alkalinity in the alkali-treated hair was measured by sampling the hair immediately after rinsing the straightener with water, extracting the residue on the hair by soaking the hair sample in water and then measuring the pH of the extraction medium as described in Example 3. For comparison, the same procedure was followed after the post-straightening texturing procedure. Surprisingly, the measurable residual alkalinity of the alkali-treated hair was lowered by texturization.

Auxiliary amounts of the texturing and strengthening agent can be applied to the virgin outgrowth before applying the hair straightener. For this purpose the texturing and strengthening agent can be provided by the same composition having a pH of at least 8 applied in a post-straightening procedure. Alternatively, a different non-acidic composition can be used. Likewise, the texturing and strengthening agent used in the post-straightening step can be the same as or different than that used in the pre-straightening step.

Auxiliary amounts of texturing and strengthening agent can be applied to previously straightened outgrowth portions of the hair contained in a non-acidic composition to augment texturing benefits.

Strengthening achieved by the method of this invention is substantially complete following the post-straightening application step. Unlike conventional procedures, therefore, the method of this invention does not depend on the use of a neutralizing shampoo for strengthening the alkali-treated hair. However, the texturizing/strengthening step can be followed, if desired, by a shampoo, with or without an intervening water rinse.

Employing a shampoo is usually preferred for purpose of cleansing and removing from the hair residual hair straightener, if any, and any excess amount of post-straightening composition from the hair or scalp. Any of a number of conventional shampoos typically used by practitioners in the hair straightening arts can be employed. Typically, such shampoos are neutralizing shampoos having an acidic to neutral pH. For purposes of practicing the principles of this invention, the type of shampoo employed need not be so limited as long as the shampoo components do not interact with or inactivate the texturing component in the hair or decrease the strength of the hair. The texturing benefits achieved by the method of this invention survived through multiple shampoo applications and were thus long-lasting effects.

Texturing and strengthening of the hair is reflected by a discernibly improved tactile feel, such as smoothness, silkiness and normally associated attributes of conditioning that influence combing, manageability, etc., as well as perceived attributes such as luster. It is generally recognized that hair condition is a complex concept that depends on a variety of physical quantities that are subjectively evaluated by practitioners. Thus, some instrumental techniques were also employed to measure functional relationships of various physical quantities of strengthening associated with subjective hair texturization properties.

One of the instrumental techniques employed measures the stress-strain modulus of hair in terms of fiber elongation and axial swelling while it is actually undergoing a chemical straightening procedure. This technique is called the intermittent modulus technique because changes in the strength of the hair under an intermittently applied additional load are measured. For this purpose, a laboratory model of an intermittent modulus device was constructed and employed.

The intermittent modulus device comprises a balance attached to a beam which controls illumination of a photocell and generates a current. Light control for the photocell is electronically regulated and current is measured on a strip chart recorder.

The instrument balance beam is attached to a test hair fiber. The hair fiber is anchored at each end by a vinyl tab and is laterally positioned. The lateral position of the fiber is controlled by a micrometer, and controls are provided on the instrument to assure exact fiber alignment. The length of the hair fiber for convenience is preferably of a gauge length of about 1.5 centimeters but is not so limited. A constant load is placed on the hair fiber and an additional load is applied at intermittent intervals. For example, a constant load of 0.5 grams can be applied, and additional loads of 0.5 grams can be applied at 30 second intervals.

Changes in the length of the fiber cause proportional changes in the position of the recorder pen. Fiber axial swelling is influenced and controlled by applied chemical treatments thus making it possible to assess the treatment in terms of fiber axial swelling. Axial swelling changes are magnified 200 times on the recorder chart, so that a 30 millimeter pen excursion is equivalent to 1 percent change in fiber length for a fiber of 1.5 centimeters gauge length.

Using this technique, therefore, fiber integrity is measured in terms of both fiber strength and fiber elongation. Fiber strength is determined by the height of the vertical pen excursion. For example, the greater the chemical attack, the weaker the fiber will become and this will be reflected by a greater vertical excursion by the pen. Fiber elongation is related to supercontraction and is reflected by changes in the vertical position of the pen on the recorder chart. Thus shortening of the fiber as it weakens is readily observable. Restoration of fiber integrity is judged as a reversal of weakened fiber strength and supercontraction, i.e., less supercontracted.

From our experience, calculated values of percent loss in tensile strength of hair that has been straightened with highly alkaline "lye" or "no-lye" relaxers obtained with the intermittent modulus technique compare favorably with those obtained by commercially available tensile testers, such as the Scott Tensile Tester, GCA/-Precision Scientific, Chicago. Ill. Also in this regard, a description of the construction of a laboratory model of an analogous device used to study the performance of depilatories can be found in Elliot, "Use of a Laboratory Model to Evaluate the factors Influencing the Performance of Depilatories," *J. Soc. Cosm. Chem.*, 25, 367 (1974).

This invention is further illustrated in the following Examples, which are not intended to be limited.

EXAMPLE 1

This example illustrates texturing and strengthening compositions suitable for use on hair that is about to undergo or has just undergone a highly alkaline hair straightening procedure. For convenience, the following formulae (A-G) contain a preferred texturing and strengthening agent, cocodimonium hydrolyzed animal protein (ingredient no. 1), and where present, a preferred cationic polymer, polyquaternium 6 (ingredient no. 2).

The compositions below are prepared by dispersing ingredients nos. 1-5 in water (ingredient 7) at a temperature of about 35 to about 45 degrees C. together with relatively slow mechanical agitation until homogeneous, cooling relatively quickly to a temperature of about 30 to about 25 degrees C. and adding ingredient no. 6 to a pH from at least 8 to about 8.5, preferably between about pH 8.1 and about 8.4.

| | Ingredient | Active Weight Percent (dry solids basis) | | | | | | |
|---|---|---|---|---|---|---|---|---|
| | | A | B | C | D | E | F | G |
| 1. | Cocodimonium hydrolyzed animal protein (Note a) | 2.4 | 2.4 | 1.2 | 2.5 | 5.0 | 3.5 | 0.2 |
| 2. | Polyquaternium 6 (Note b) | 1.2 | 1.2 | — | — | 5.0 | 0.1 | — |
| 3. | Polysorbate-20 (Note c) | 1.0 | — | — | 0.5 | — | — | — |
| 4. | DL-Panthenol | — | 1.0 | — | — | — | — | — |
| 5. | Preservative | Q.S. | | | | | | |
| 6. | Triethanolamine (85% in water) to pH 8-8.5 | Q.S. | | | | | | |
| 7. | Water, deionized, to 100 percent | Q.S. | | | | | | |

Note a: CTFA adopted name for a coconut dimethyl ammonium derivative of hydrolyzed collagen protein sold under the trade name CROQUAT M by Croda, Inc., supplied as a 40 percent solution in water, and staed to have an approximate molecular weight of 2,500.

Note b: CTFA adopted name for poly(dimethyldiallyl ammonium chloride) corresponding to the material sold under the trade name MERQUAT-100 by Merck Chemical Division, Merck & Company, Inc., supplied as a 40 percent solution in water, and stated by the manufacturer to have a weight average molecular weight of approximately 100,000.

Note c: CTFA adopted name for polyoxyethylene (20) sorbitan monolaurate, a nonionic emulsifier.

EXAMPLE 2

This example illustrates nonacidic compositions suitable for use in applying auxiliary amounts of texturing and strengthening agent to hair that is about to undergo a highly alkaline hair straightening procedure. For convenience, the same preferred texturing and strengthening agent and preferred cationic polymer used in Example 1 are employed.

| | Ingredient | Active Weight Percent (dry solids basis) | | | | | | |
|---|---|---|---|---|---|---|---|---|
| | | H | I | J | K | L | M | N |
| 1. | Cocodimonium hydrolyzed animal protein (Note a, Example 1) | 0.2 | 0.8 | 1.2 | 0.25 | 1.0 | 3.5 | 1.5 |
| 2. | Steartrimonium hydrolyzed animal protein (Note d) | 0.45 | 0.45 | 0.45 | 0.5 | 0.5 | — | — |
| 3. | Dicetyldimonium chloride (Note e) | 1.5 | 0.75 | 0.75 | 1.5 | — | 0.2 | — |
| 4. | Polyquaternium 6 (Note b, Example 1) | 0.2 | 0.4 | 0.02 | 0.25 | — | 0.1 | 1.0 |
| 5. | Cetearyl Alcohol (and) Ceteareth-20 (Note f) | 2.0 | 2.0 | 2.0 | 2.0 | 1.5 | 0.5 | — |
| 6. | Emulsifying Wax-NF (Note g) | 2.0 | 2.0 | 2.0 | 2.0 | — | 1.0 | — |
| 7. | Propylene glycol | 25.0 | 25.0 | 25.0 | 25.0 | — | — | — |
| 8. | Preservative | Q.S. | | | | | | |
| 9. | Water, deionized, | Q.S. | | | | | | |

-continued

| | Active Weight Percent (dry solids basis) | | | | | |
|---|---|---|---|---|---|---|
| Ingredient | H | I | J | K | L | M | N |
| to 100 percent | | | | | | | |

Note d: CTFA adopted name for a stearyltrimethyl ammonium derivative of hydrolyzed collagen sold under the trade name CROTEIN Q by Croda, Inc., supplied as a 90 percent active powder, and stated to have an approximate molecular weight of 12,000.
Note e: CTFA adopted name for N-hexadecyl-N,N-dimethyl-1-hexadecaminium chloride corresponding to the material sold under the trade name ADOGEN 432 CG by Sherex Chemical Co., Inc. supplied as a 75 percent solution in water.
Note f: CTFA adopted name corresponding to a nonionic emulsifier sold under the name Promulgen D by Amerchol Corporation.
Note g: CTFA adopted name corresponding to a nonionic emulsifier that is a mixture of higher fatty alcohols and ethylene oxide sold under the trade name Polawax Regular by Croda, Inc.

The compositions are prepared by dispersing all ingredients, except nos. 2 and 3 in water at a temperature of about 80 degrees C. with gentle mechanical agitation until homogeneous, cooling the solution relatively quickly to about 50 degrees C. and adding ingradients nos. 2 and 3. Mechanical agitation is maintained until the composition has cooled to about 25 degree C.

EXAMPLE 3

This example illustrates the post-straightening benefit of texturing and strengthening hair that has just undergone a highly alkaline hair straightening procedure by applying a nonacidic composition of this invention without increasing the residual alkalinity of the alkali-treated hair.

For this study, a commercial "no-base" type hair straightener product of regular strength containing about 2 to about 2.5 percent sodium hydroxide (C) was employed. Eleven female volunteers, each having varying degrees of natural curl in their hair had their hair straightened in the following procedure.

Because each of the volunteers had a history of previous chemical straightening of their hair, the nonvirgin outgrowth portion was treated with a pre-straightening auxiliary amount of texturing and strengthening composition. The hair was parted into four sections from the forehead to the nape and then across the head from ear to ear. Approximately 5 milliliters of the non-acidic composition H of example 2 was applied to each sectioned outgrowth portion and distributed by combing to contact the fibers from the start of the outgrowth portion to the tip ends. A total of about ¼ ounce to about ½ ounce of composition was applied to the entire head of hair depending on each subject's needs.

The straightener product was applied to the virgin curly new growth portions of the hair in the conventional manner following the manufacturer's instructions. For subjects having hair characterized as fine, medium and coarse, the respective total contact time with the highly alkaline chemical hair straightener was about 13 minutes, about 15 minutes and about 18 minutes, respectively.

When the desired amount of straightening was obtained, the hair was rinsed with water thoroughly until substantially all visible traces of the straightener product were removed from the hair and scalp. Excess water was squeezed from the hair and immediately afterwards, several relatively small tresses totaling at least about 250 milligrams (mg) of hair were sampled by cutting them from randomly selected scalp areas. The cut tresses were pooled, identified as "after relaxer" samples and allowed to air dry at ambient room temperature and humidity.

The hair having just undergone alkali-straightening as well as the outgrowth portion was then treated with a post-straightening amount of texturing and strengthening agent using composition A of Example 1. This composition was clear and had a pH of 8.3. Approximately one ounce of texturing composition was applied to the hair and was gently combed through from the crown to the nape to contact all portions of the hair fibers. After about 5 minutes, several relatively small tresses of hair were again randomly sampled as described earlier. The pooled samples were identified as "after texturing" and were allowed to air dry at ambient room temperature and humidity. Except for the removal of hair samples as described above, each of the volunteers had their hair subsequently shampooed with a commercial non-alkaline neutralizing shampoo (E) and styles as practiced in conventional procedures. The neutralizing shampoo contained an amphoteric surfecant and had a pH of about 5.5 to about 6.5.

The residual alkalinity of the sampled hair identified above was measured by soaking the hair in deaerated distilled water and measuring the pH of the extraction medium using the following procedure. The deaerated distilled water was prepared by boiling distilled water (Hinckley & Schmidt) and then cooling it to ambient room temperature just before using it. For measuring pH, a Radiometer model TTA60 titration assembly was used in conjunction with a Radiometer model PHM64 research pH meter.

After the hair sampled had dried, it was prepared for pH measurements by cutting an individually indentified tress into a relatively fine size and thoroughly mixing the cutting to obtain a substantially uniformly distributed sample. An amount of about 300 to about 500 mg of this finely cut hair was accurately weighed into a titration vessel adapted for use with the Radiometer titration assembly, covered lightly and set aside until needed. This procedure was followed for all tresses obtained, retaining each identified sample in separate vessels. For comparison purposes, the amount of finely cut hair weighed for measuring the residual alkalinity after the relaxer step and after the texturing step was about the same, where possible.

A volumetric amount of 10 milliliters of the distilled water, prepared as described above, was pipetted into an empty dry titration vessel, mounted on the titration assembly and stirred for 10 minutes. The pH of the water was measured at the end of the 10 minutes and recorded. This procedure was repeated several times during the course of this study to determine the average pH of the water using separate vessels for each measurement. Based on these measurements, the average pH value of the water was about 6.18.

To measure the residual alkalinity of the hair sampled and identified as "after relaxer", 10 milliliters of the deaerated distilled water described above were volumetrically pipetted into the titration vessel containing the accurately weighed finely cut hair sample. This vessel was then mounted on the titration assembly and the hair/water mixture was stirred for 10 minutes, after which the pH of the extraction medium was measured and recorded. The procedure was repeated with a second sample and the average pH value of the duplicate samples was determined. The individual pH values between duplicates agreed within 0.1 pH unit. This same procedure was followed for hair sampled and indentified as "after texturing."

The average pH values of the extraction medium obtained from the amount of hair sampled taken from each of the eleven volunteers (1-11) are compared in the following Table.

| | Average pH of Medium | | | | |
|---|---|---|---|---|---|
| | (A) | | (B) | | |
| Volunteer | Mg Hair | After Relaxer | Mg Hair | After Texturing | (A-B) Change |
| 1 | 500 | 7.62 | 500 | 7.16 | −0.46 |
| 2 | 500 | 8.13 | 500 | 7.71 | −0.42 |
| 3 | 337 | 9.26 | 339 | 8.60 | −0.66 |
| 4 | 500 | 9.12 | 500 | 7.70 | −1.42 |
| 5 | 372 | 8.92 | 320 | 7.59 | −1.33 |
| 6 | 500 | 9.14 | 500 | 7.33 | −1.81 |
| 7 | 500 | 9.26 | 271 | 7.37 | −1.89 |
| 8 | 358 | 9.14 | 316 | 8.24 | −0.90 |
| 9 | 309 | 9.44 | 401 | 7.76 | −1.68 |
| 10 | 500 | 9.30 | 500 | 8.40 | −0.90 |
| 11 | 423 | 7.84 | 353 | 7.55 | −0.29 |
| Average | | 8.83 | | 7.76 | −1.07 |

The overall variation between the pH values obtained for any two separate volunteers can be attributed to differences expected for variable rinsing times used by the beautician as required for that individual volunteer.

The results show that the residual alkalinity on the alkali-straightened hair was decreased by the texturing and strengthening composition. As seen, in all cases the residual alkalinity of the medium for textured hair samples (column B) was lower than that of the medium for relaxed hair sample (column A), by from 0.29 to 1.89 pH units with a average decrease of about one pH unit. Thus, at the end of the texturing and strengthening procedure, the alkalinity of the residue on the textured hair was substantially neutral (average value of pH 7.76) whereas after the relaxer, it was alkaline (average value pH 8.83).

EXAMPLE 4

This example illustrates the texturing benefit of the method of this invention using a nonacidic texturing and strengthening composition of this invention (A) compared to that of an acidic commercial "normalizer" product (B) embodying the principles of U.S. Pat. No. 4,602,648.

The general procedure of Example 3 was followed, except that no hair tresses were sampled. For comparison purposes, the same procedure of Example 3 was practiced on one side of the head (identified as side A) employing composition H of Example 2 as the auxiliary texturing and strengthening agent before applying the commercial regular strength straightener product (C), and composition B of Example 1 having a pH of 8.15 as the post-straightening texturing and strengthening composition. The amounts applied to the hair were adjusted accordingly as needed.

On the opposite side of the head (identified as side B) the hair was straightened, following the manufacturer's instruction using the regular strength hair straightener product component (D) supplied with the acidic pre-shampoo normalizer product (B). The amounts applied were adjusted for half-head usage. Following instructions, the pre-shampoo normalizer product (B) was applied to the hair after rinsing the hair straightener product (D) from the hair with water, massaged through the hair gently. After a period of about 5 minutes the hair was shampooed. The same neutralizing shampoo (E) was employed on both sides of the head. Multiple shampoo application of at least two to three were employed, as needed.

Experienced beauticians evaluated and compared the characteristics of the products and the texture and strength of the hair as shown below in a study using 50 female volunteer subjects.

| | Number of Notations | | |
|---|---|---|---|
| Characteristic | Side A | Side B | No Diff. |
| Softer feel on wet hair after post-straightener treatment | 43 | — | 7 |
| Easier wet combing after shampooing | 44 | 1 | 5 |
| Hair loss (more breakage) | — | 3 | 47 |
| Easier dry combing | 1 | — | 44 |
| Preferred dry feel of hair | 6 | — | 40 |
| More straightening | 7 | 5 | 38 |
| Sheen | — | — | 50 |
| Manageability | — | — | 50 |
| Static flyaway | — | — | 50 |
| Overall preferred | 36 | 4 | 10 |
| Alkali sensation on scalp | 6 | 13 | — |

The results show that applying a texturing and strengthening agent of this invention contained in a nonacidic composition to hair about to undergo and to hair having just undergone a highly alkaline hair straightening procedure provided more discernible conditioning benefits than did a commercial product employing an acidic pre-shampoo normalizer composition. These benefits show that the texturing effect survived multiple shampoo applications.

EXAMPLE 5

This example illustrates the benefit of strengthening hair undergoing a highly alkaline hair straightening procedure with nonacidic texturing and strengthening compositions of this invention. Strengthening was determined by intermittent modulus technique using the intermittent modulus device described above.

For this study, fibers of natural brown-colored intact hair (R. Weintraub, New York, N.Y.) of gauge length 1.5 centimeters were individually mounted between vinyl tabs. A constant load of 0.5 grams was used with an additional intermittent load of 0.5 grams applied at 30 second intervals. Restoration of fiber integrity was determined by observing changes in the strength and elongation (supercontraction) of the fiber undergoing the hair straightening procedure. These changes were recorded on a Heath strip chart recorder having a 10 millivolt sensitivity using a chart speed of 0.1 inches per minute. A 30 millimeter pen excursion for this length fiber was equivalent to a 1 percent change in fiber length. For example, the strength of the fiber weakened and supercontracted during a relaxer treatment as reflected by changes in the vertical position of the pen on the chart. Thus, strenthening was determined by observing reversals in this pattern, based on proportional changes in the recorder pen position.

A series of studies were made to observe the strengthening effects of applying nonacidic compositions of this invention to the hair at various stages of the hair straightening procedure. In all studies, the relaxer product used was the commercial regular strength sodium hydroxide containing relaxer creme (C) of Example 3, applied as supplied in an amount sufficient to coat the fiber, left on the hair to the point where maximum supercontraction was recorded (usually about 3 to about 5 minutes), after which the relaxer was rinsed from the fiber with tap water.

The variations in the process were either in stage (I) where the hair about to undergo straightening was pretexturized by applying the nonacidic composition H (pH 6.1) of Example 2 immediately before the relaxer, or in stage (II) where the hair having just undergone straightening was texturized by coating the fiber with nonacidic composition A (pH 8.32) of Example 1 for about 5 minutes, or in stage (III) where the post-straightening texturization procedure in stage (II) was followed by a tap water rinse (WR) or in stage (IV) where the entire procedure was terminated by shampooing with the commercial nonalkaline neutralizing shampoo (S) of Example 3, except that the shampoo was diluted 1:9 parts with tap water for convenience.

These variations are summarized in the following Table in study nos. 1-6. For comparison, study nos. 7-9 were included to observe the strengthening effects achieved by practicing the principles taught in the '648 patent by substituting the commercial acidic normalizer product (N) used in Example 4 in stage (II). For further comparison, a counterpart to the acidic normalizer containing the texturing and strengthening agent of this invention (composition T, pH 3.5) was prepared for use in stage (II) shown in study no. 10.

Composition T was prepared following the procedure of Example 1 for composition B, except that triethanolamine was omitted and instead included 0.5 weight percent boric acid and 0.2 weight percent citric acid along with 0.2 weight percent of a polyquaternium 10 having an average molecular weight of about 100,000. (Polyquaternium 10 is the CTFA adopted name for a polymeric quaternary ammonium salt of hydroxyethyl cellulose reacted with a trimethyl ammonium substituted epoxide corresponding in this instance to Polymer JR 30M sold by Union Carbide Company.) Each study shown in the Table was done in duplicate. The stage performed is shown by the alphabetical designation of the composition used while the omission of the stage is indicated by a dash.

| Study no. | Stage I | Stage II | Stage III | Stage IV |
|---|---|---|---|---|
| 1 | — | — | — | S |
| 2 | — | A | WR | — |
| 3 | H | — | — | — |
| 4 | H | A | WR | — |
| 5 | H | — | — | S |
| 6 | H | A | — | S |
| 7 | — | N | — | S |
| 8 | H | N | WR | S |
| 9 | H | N | WR | — |
| 10 | — | T | WR | — |

The results showed that water rinsing alkali-straightened hair, in itself, strengthens the alkali weakened fiber to a certain extent, and that an acidic neutralizing shampoo, as in study no. 1 contributes further to producing a less supercontracted, i.e., less rubbery, more springy, fiber. This result and study generally agrees with what is conventionally practiced and known.

More importantly, the study also confirmed that the texturing and strengthening agent of this invention applied to the hair in stage II strengthened the hair and that strengthening was substantially completed at the end of stage II. The strengthening achieved was substantially equivalent to that provided upon use of an acidic neutralizing shampoo. Thus, the neutralizing shampoo step in Stage IV provided no further increased strength benefit, based on study nos. 2, 4, and 6. Additionally, the strengthening effect obtained was unaffected by rinsing with water after the texturing procedure.

Any measurable benefit of the texturing and strenthening agent on fiber properties applied in stage I was generally obscured by the overwhelming weakening effect of the relaxer in study nos. 3, 4, 5 and 6. This result showed that the nonacidic composition H did not interfere with the straightening action of the relaxer even though the measurable pH of composition H was inherently mildly acidic (pH 6.1). While this study was unable to detect strengthening benefits from applying this particular nonacidic composition, we know from experience and the texturing results in Example 4 show that composition H contributes to augmenting the texturing effect on the hair.

The texturing and strengthening agent of this invention generally showed a pattern of strengthening seen on the recorder as a gradual increase in fiber length that leveled off when complete. Thus, while the mechanism is not fully understood, the result suggests that the cation receptive negative sites in the hair are sustained while the nonacidic composition of this invention simultaneously strengthens and texturizes the hair in stage II. A similar gradual pattern was seen in study no. 10 where the composition was purposely acidified. The result confirms that strengthening is substantially as effective as an acidic neutralizer.

This observation was further confirmed when the commercial normalizer product N was used instead in stage II in study nos. 7-9. The pH of this product was measured as pH 4.6. Unlike the nonacidic texturing and straightening compositions of this invention, product N reversed supercontraction of the relaxed hair relatively rapidly but strengthening overall was not superior to that obtained with the strengthening agent in composition A of the invention. This result suggests that the acid components in product N deswell the fiber rapidly owing to acid neutralization of the alkaline residue on the hair as one would expect. However, any benefit achieved from such rapid reversal in terms of lasting conditioning was not observed as shown in Example 4.

In another study, the procedure of study no. 5 was repeated except the commercial regular strength relaxer used contained a cationic polymer along with sodium hydroxide (CP). Strengthening effects observed were similar to those of Study no. 5.

EXAMPLE 6

This example illustrates nonacidic compositions having a pH of at least 8 to about 8.5 suitable for use in applying texturing and strengthening agent in an auxiliary amount in a pre-straightening step or in a post-straightening step or in both steps to hair undergoing an alkaline hair straightening procedure.

| Ingredient | Active Weight Percent (dry solids basis) | | | | | |
|---|---|---|---|---|---|---|
|  | O | P | Q | R | S | T |
| 1. Cocodimonium hydrolyzed animal protein (Note a, Example 1) | — | 2.4 | 2.4 | 2.4 | 2.0 | — |
| 2. Steartrimonium hydrolyzed animal protein (Note d, Example 2) | 2.4 | 0.9 | 0.9 | 0.9 | 1.0 | — |
| 3. Dicetyldimonium | — | 1.5 | 1.5 | 1.5 | 1.5 | 1.5 |

-continued

| Ingredient | Active Weight Percent (dry solids basis) | | | | | |
|---|---|---|---|---|---|---|
| | O | P | Q | R | S | T |
| chloride (Note e, Example 2) | | | | | | |
| 4. Polyquaternium 6 (Note b, Example 1) | 1.2 | 1.2 | 1.2 | 1.2 | 1.0 | 1.5 |
| 5. N-soya-N-ethyl morpholinium ethosulfate (Note h) | — | 0.5 | — | — | — | 0.5 |
| 6. Hydrolyzed animal protein (Note i) | — | 2.2 | 2.2 | — | — | — |
| 7. Cetearyl Alcohol (and) Ceteareth-20 (Note e, Example 2) | — | 2.0 | 2.0 | 2.0 | 2.0 | 2.0 |
| 8. Emulsifying Wax-NF (Note f, Example 2) | — | 2.0 | 2.0 | 2.0 | 2.0 | 2.0 |
| 9. Stearic Acid | — | 1.5 | — | — | 1.0 | 1.5 |
| 10. Propylene glycol | — | 15.0 | — | — | 10.0 | 15.0 |
| 11. Preservative | | | Q.S. | | | |
| 12. Thickener | Q.S. | — | Q.S. | Q.S. | Q.S. | Q.S. |
| 13. Triethanolamine (85% in water) to pH 8–8.5 | | | Q.S. | | | |
| 14. Water, deionized to 100 percent | | | Q.S. | | | |

Note h: Such as ATLAS G-271 sold by ICI Americas, Inc. as a 35 percent aqueous solution.
Note i: CTFA adopted name for a hydrolyzed animal protein sold under the trade name LEXEIN X250 by Inolex Chemical Company, supplied as a 55 percent aqueous solution.

EXAMPLE 7

This example illustrates the benefit of strengthening hair undergoing a highly alkaline hair straightening procedure with non-acidic texturing and strengthening compositions of this invention applied in a texturing procedure practiced in a pre-straightening step and in a post-straightening step. Strengthening was determined by tensile wet break strength technique as described below.

For this study (No. 1) a 5-inch tress of natural dark brown hair (DeMeo Brothers, New York, N.Y.) 2 grams in weight was used. To this tress, 5 grams of the commercial regular strength hair straightener C used in Example 3 was applied. After 18 minutes, the hair straightener was removed by thoroughly rinsing the hair tress using warm tap water (Stage 1). The texturing and straightening composition A of Example 1 was applied in an amount of 1 gram to the rinsed straightened hair. After 5 minutes, the composition was rinsed from the hair using warm tap water (Stage 2).

The tensile wet elongation and break strength of the textured tress was determined by removing 25 fibers from the tress after Stage 1 and again after Stage 2. The fibers were equilibrated in water overnight. The gram force required to break the wet fiber under elongation while submerged in water was measured using the Scott Tensile Tester, and mean break force determined. For comparison, fibers from an untreated tress were similarly tested as a control.

In another study (No. 2), the procedure of study No. 1 was repeated, excepted that 0.5 grams of auxiliary texturing and straightening composition B of Example 2, was also applied to the tress immediately before applying the hair straightener.

For comparison a regular straightening procedure was practiced in a third study (No. 3) in which 5 grams of the commercial regular strength hair straightener containing cationic polymer CP used in Example 3 was applied to a similar tress and the procedure of Study No. 1 up to Stage 1 otherwise followed. After rinsing the hair straightener from the hair, the straightened hair was shampooed using two sudsings with the non-alkaline neutralizing shampoo E of Example 3, rinsing thoroughly (Stage 3). The results in the following table show the percent decrease in strength after straightening (Stage 1), and either after post-straightening tensile texturing (Stage 2) or after neutralizing (Stage 3) and the percent regain in original pre-strengthened strength.

| Study No. | A Mean Tensile Gram Break Force | B Percent Decrease in Strength | Percent Regain in Strength |
|---|---|---|---|
| 1 (Stage 1) | 43.48 | −17.79 | — |
| 1 (Stage 2) | 50.48 | −4.55 | 75 |
| 2 (Stage 1) | 47.87 | −9.46 | — |
| 2 (Stage 2) | 53.00 | +0.21 | 100 |
| 3 (Stage 1) | 44.09 | −16.64 | — |
| 3 (Stage 3) | 48.82 | −7.70 | 50 |
| Untreated (Control) | 52.9 | — | 0 |

The data were found statistically significant at a confidence level of 95 percent when subjected to a Standard Statistical T-Test Analysis.

The break strength results of Study No. 1 showed that the texturing compositions of this invention restored tensile strength to the alkali-straightened hair to a level approaching the original pre-straightened level when applied in a post-straightening procedure. In study No. 2, the original tensile strength of the hair was substantially regained when auxiliary texturing composition was applied in a pre-straightening step as well. This finding showed that the texturing procedure provided a lasting protective effect.

By applying auxiliary texturing composition before straightening, the decrease in tensile strength caused by the alkaline hair straightener was lessened by about 8.33 percent comparing stages 1 of Studies No. 1 and No. 2.

The results further show that the texturing and strengthening compositions in the method of this invention restored tensile strength to a greater extent than was restored by a non-alkaline neutralizing shampoo in Study No. 3.

The present invention has been described with respect to preferred embodiments. It will be clear to those skilled in the art that modifications and/or variations of the disclosed compositions and methods can be made without departing from the scope of the invention set forth herein.

What is claimed is:

1. An aqueous hair texturing and strengthening composition for application to hair about to undergo a highly alkaline hair straightening procedure comprising an aqueous nonacidic cosmetic vehicle having dispersed therein about 0.1 to about 8 weight percent on a total composition weight basis of at least one water-dispersible quaternary nitrogen-containing compound having at least one alkyl group directly or indirectly bonded to a quaternary nitrogen group, each said alkyl group containing about 3 to about 22 carbon atoms, each said compound being selected from the group consisting of (a) non-proteinaceous, non-polymeric quaternary nitrogen containing compounds which are in the salt form and which contain said alkyl group and (b) hydrolyzed proteins which are in the salt form wherein at least one amino group therein is quaternized to include said alkyl group, each said compound being characterized by having a positive charge and being stable when in an aqueous medium at a pH of at least about 6.1.

2. The composition of claim 1 which additionally includes from zero to about 5 weight percent on a total composition basis of a dispersed cationic polymer having a weight average molecular weight of about 3,000 to about 10,000,000.

3. The composition of claim 1 wherein said non-proteinaceous, non-polymeric quaternary nitrogen containing compound contains an alkyl group that is derived from a fatty acid.

4. The composition of claim 1 wherein said non-proteinaceous, non-polymeric quaternary nitrogen containing compound is dicetyldimonium chloride.

5. The composition of claim 1 wherein said hydrolyzed protein is a hydrolyzed collagen protein in which over 70 percent of the available amino groups have each been quaternized to incorporate at least one alkyl group containing about 3 to about 18 carbon atoms each.

6. The composition of claim 5 wherein said quaternized hydrolyzed collagen protein has a weight average molecular weight of about 2500 to about 12,000 and an isoionic point of about 9.5 to about 11.5, and said alkyl groups thereof each contain about 12 to about 18 carbon atoms.

7. The composition of claim 1 wherein said hydrolyzed protein is a hydrolyzed animal protein having at least one alkyl group containing about 12 to about 18 carbon atoms.

8. The composition of claim 1 wherein said hydrolyzed protein is cocodimonium hydrolyzed animal protein.

9. The composition of claim 1 wherein said hydrolyzed protein is steartrimonium hydrolyzed animal protein.

10. The composition of claim 1 wherein said salt form has an anion selected from the group consisting of halides, sulfate, sulfite, phosphate, nitrate, nitrite, acetate, methylsulfate, ethosulfate and toluenesulfonate.

11. The composition of claim 1 having a pH of about 6.1.

12. A method for straightening hair comprising the steps of:
    (a) first applying to the hair a composition of claim 1;
    (b) then applying to the resulting hair a highly alkaline hair straightener for a time sufficient to at least partially straighten said hair;
    (c) rinsing substantially all of said straightener from said so straightened hair; and
    (d) washing said so rinsed hair with a neutralizing shampoo having a neutral to acidic pH.

13. The method of claim 12 wherein the applied composition in step (a) has a pH of at least about 6.1.

14. The method of claim 12 wherein the applied composition in step (a) additionally contains about 0.1 to about 3.5 weight percent of a water-dispersible cationic polymer having a weight average molecular weight of about 3,000 to about 10,000,000.

15. The method of claim 12 wherein after said rinsing and before said washing, said so rinsed hair is contacted with an aqueous hair conditioning composition.

16. The method of claim 15 wherein said aqueous hair conditioning composition is an aqueous hair texturing and strengthening composition of claim 1.

17. The method of claim 16 wherein said aqueous hair texturing and strengthening composition has a pH of at least about 8.

18. The method of claim 16 wherein the composition applied in step (a) has a pH of about 6.1.

* * * * *

UNITED STATES PATENT AND TRADEMARK OFFICE
CERTIFICATE OF CORRECTION

PATENT NO. : 5,148,822
DATED : September 22, 1992
INVENTOR(S) : Muhammad Akhtar

It is certified that error appears in the above-identified patent and that said Letters Patent is hereby corrected as shown below:

Col. 14, line 29 change "staed" to --stated--.

Col. 14, line 30 change "2.500" to --2,500--.

Col. 14, line 52 in the chart under column K, change "0.25" to --2.5--.

Col. 16, line 19, change "styles" to --styled--.

Col. 16, line 20, change "surfecant" to --surfactant--.

Signed and Sealed this

Twenty-third Day of November, 1993

Attest:

BRUCE LEHMAN

Attesting Officer

Commissioner of Patents and Trademarks